(12) United States Patent
Chang

(10) Patent No.: US 6,685,930 B1
(45) Date of Patent: Feb. 3, 2004

(54) METHODS AND SUBSTANCES FOR RECRUITING THERAPEUTIC AGENTS TO SOLID TUMORS

(75) Inventor: Tse Wen Chang, Hsin-Chu (TW)

(73) Assignee: Tanox, Inc., Houston, TX (US)

( * ) Notice: Subject to any disclaimer, the term of this patent is extended or adjusted under 35 U.S.C. 154(b) by 1733 days.

(21) Appl. No.: 08/855,744

(22) Filed: May 8, 1997

Related U.S. Application Data

(63) Continuation of application No. 08/264,649, filed on Jun. 23, 1994, now abandoned, which is a continuation of application No. 07/675,654, filed on Mar. 27, 1991, now abandoned.

(51) Int. Cl.[7] ..................... A61K 45/00; A61K 39/395; A61K 9/127
(52) U.S. Cl. ................ 424/85.2; 424/136.1; 424/152.1; 424/450
(58) Field of Search .............. 424/85.1, 85.2, 424/134.1, 135.1, 136, 450

(56) References Cited

U.S. PATENT DOCUMENTS

| | | | | |
|---|---|---|---|---|
| 4,946,778 A | | 8/1990 | Ladner et al. ............. 435/69.6 |
| 4,957,735 A | * | 9/1990 | Huang ....................... 424/85.8 |
| 4,980,160 A | * | 12/1990 | Goldberg et al. .......... 424/85.1 |
| 5,091,313 A | * | 2/1992 | Chang ..................... 530/387.9 |
| 5,091,513 A | | 2/1992 | Huston et al. ........... 530/387.3 |
| 5,091,542 A | * | 2/1992 | Ahlem et al. ............... 548/521 |
| 5,132,405 A | | 7/1992 | Huston et al. ........... 530/387.3 |
| 5,149,782 A | * | 9/1992 | Chang et al. ............... 530/326 |
| 5,200,176 A | * | 4/1993 | Wong et al. ................ 424/85.1 |
| 5,211,945 A | * | 5/1993 | Wallach et al. ............ 424/85.1 |

FOREIGN PATENT DOCUMENTS

| | | | |
|---|---|---|---|
| EP | 0263046 | * | 4/1988 |
| WO | WO8500522 | | 7/1984 |
| WO | 8809344 | * | 12/1988 |
| WO | 8911863 | * | 12/1989 |

OTHER PUBLICATIONS

Bird et al (1988) Science 242:423–426.*
Huston et al (1988) PNAS USA 85:5879–5883.*
Colcheu et al (1990) J. Natl. Cancer Inst. 82:1191–1197.*
Allean et al (1988) J Interferon Res 8:25–33.*
Glennie et al (1987) J. Immunol 139:2367–75.*
Goodwin (1987) J. Nucl. Med. 28(8):1358–1362.*
Goodwin et al (1988) J. Nucl. Med 29:226–234.*
Bird et al, Trends in Biotechnology 9:132–37 (1991).
Chaudhary, Nature 339:394–97 (1989).
Abstract med line 86293741 of G Biochem. Biophys. Res. Common. 138(2):611–17(1986).

* cited by examiner

*Primary Examiner*—Ponnathapu Achutamurthy
*Assistant Examiner*—David J. Steadman
(74) *Attorney, Agent, or Firm*—Cheryl A. Liljestrand

(57) ABSTRACT

Disclosed is a method of using bifunctional binding molecules, such as two linked $V_H$–$V_L$ single chain binding molecules, to recruit a therapeutic agent to a solid tissue site. The therapeutic agent is administered separately from the binding molecules and following the administration of a remover substance which aids in clearing free binding molecules in the circulation. In the preferred mode of the invention, the binding molecules have one specificity for antigens at the target site and one for the therapeutic agent. The binding molecules are administered and allowed time to approach a maximum concentration in the extravascular space. A remover substance, preferably a liposome conjugated with antibodies which are reactive with an antigenic epitope on the binding molecules, is then administered to remove excess binding molecules from the circulation and the extravascular space. A therapeutic agent, preferably a cytotoxic drug such as ricin A chain modified so as to enable it to enter the target cells once delivered to the target site, is then administered.

2 Claims, 3 Drawing Sheets

METHODS AND SUBSTANCES FOR RECRUITING THERAPEUTIC AGENTS TO SOLID TUMORS

This is a continuation of application Ser. No. 08/264,649 filed on Jun. 23, 1994, abandoned, which was a continuation of application Ser. No. 07/675,654, filed Mar. 27, 1991, abandoned.

FIELD OF THE INVENTION

The invention relates to using bifunctional two-domain binding molecules to recruit therapeutic agent to a solid tissue site, wherein the bifunctional binding molecules are administered first, and once the binding molecules reach maximum concentration in the extravascular space, a remover substance is administered to aid in clearing the binding molecules in the blood circulation and extravascular space, and thereafter, the therapeutic agent is administered.

BACKGROUND OF THE INVENTION

Much research and experimentation has been done on how to deliver therapeutic and imaging agents to solid tissue sites in vivo. Such site-specific delivery has often been attempted with monoclonal antibodies ("mAbs") conjugated with the therapeutic or imaging agents. These immunoconjugates are often called "magic bullets", because of their ability to specifically target diseased or tumorous sites in vivo.

Immunotoxins, which are immunoconjugates in which mAbs are conjugated with toxic substances, such as plant or bacterial-derived toxins including pseudomonas exotoxin, ribosomal-inactivating proteins, ricin, gelonin, and pokeweed antiviral peptide, have also been extensively studied. Additionally, mAbs conjugated with metal-chelating agents, where the metal-chelating agents can carry radioactive isotopes, have been used for both treating and imaging tumors.

Immunoconjugates, and particularly immunotoxins, have been actively investigated for treatment of tumors both in solid tissue and in other areas. Clinical trials of immunotoxins for removing tumors or decreasing tumor loads have been conducted. Such tests have often been with immunotoxins where the mAb is conjugated with the A chain of ricin or a radioactive isotope. Immunotoxins have also been studied in animal models for eliminating malignant cells in tumors transplanted into the animals.

These studies indicate that immunotoxins are more effective in treating leukemia or lymphoma than solid tumors. One plausible explanation for this difference in efficacy is that malignant cells in blood or lymphoid tissues are more accessible than those in solid tumors. Thus, many malignant cells in a solid tumor come in contact only with insufficient amounts of toxin to kill them. In addition, even where the toxin is in contact with the target cells, only a very small fraction will actually enter the cell and thus, not all cells in a solid tumor will be killed.

It is possible, of course, to increase the total amount of immunotoxin administered, in order to increase that which is in the vicinity of malignant cells and available to kill the cells. However, because of the conjugation with the antibody molecules, much of the immunotoxin is also absorbed and taken up by the reticuloendothelial cells of the body. The toxin will damage or destroy these cells. Specifically, a large proportion of immunotoxin ends up in the phagocytic cells in the liver, where, because of its toxicity, it can damage the liver and its function. Thus, the total amount of toxin which can be administered is severly limited.

An illustration of the problems encountered with immunotoxins is seen in a typical clinical trial. See Parker, S. A. et al. "Therapeutic Monoclonal Antibodies" Ed. by Borrebaeck, C. A. and Larrick, J. W. pp. 127–141 (Stockton Press, New York 1990). Patients with B cell lymphoma were treated with anti-idiotype antibodies coupled with the radioactive isotype $^{90}$Yttrium. This therapy proved so toxic that the immunoconjugate had to be administered with excess cold, unlabeled anti-idiotype antibodies. However, the excess cold anti-idiotypes competed with the labeled immunoconjugates for binding to the tumor associated antigen, and thereby inhibited the binding of the immunoconjugates to the tumor cell targets.

Similar drawbacks result where an immunoconjugate which includes a mAb and a radioactive isotype is used for tumor imaging. The immunoconjugate tends to be bound and taken up in phagocytic cells in the liver, spleen, and blood circulation, because the antibody portion of the immunoconjugate is absorbed by these cells. This increases the background "noise" and interferes with tumor imaging, and it can also cause toxic levels of radioactivity in all of these organs.

Several groups have tried to solve the major problem which results when using mAbs coupled with imaging agents, ie., the imaging agent is absorbed in vivo and cleared together with the antibody. One group suggested that instead of coupling the mAbs and the imaging agents, a bispecific antibody, which is not coupled to an imaging agent, should be administered first. The bispecific antibody has one specificity against the tumor being targeted and the other against a chelate conjugated to a peptide. The bispecific antibody distributes between the tumor and the circulation, and at a point when there is a high tumor-to-background ratio, a labeled chelate is administered. The chelate which is not absorbed by the antibody is rapidly excreted by the kidneys, due to its relatively small size. This results in low background noise. See *Monoclonal Antibodies in Immunoscintigraphy* Ed. by Chatal, J. F., pp. 70–71 (CRC Press, Boca Raton, Fla. 1989).

Another group discussed administering an antibody which slowly diffuses to the target tumor, and then clearing the excess circulating antibody. The clearance is done with an antigen covalently bound to a slowly diffusable serum protein (human transferrin). Thereafter, the imaging tracer is administered as an epitopically derivatized bifunctional chelate which is small and rapidly diffusable, and quickly cleared. Again, this is designed to help reduce background radiation and improve imaging. See Goodwin, D. A. et al., *J. Nuc. Med.* 29:226–34 (1988). A related paper suggested using bifunctional antibodies such as two Fab' fragments coupled at the SH groups, where one specificity is for the chelate and the other is for the tumor site antigen. See Goodwin, D. A., *J. Nuc. Med.* 28:1358–62 (1987).

Another related paper suggested injecting antibody and labeled protein (transferrin) followed by injection of anti-human IgG antibody and anti-transferrin antibody. The second antibody injection helps to clear excess labeled transferrin and reduce the background noise. See Goodwin, D. A. et al., *J. Nuc. Med.* 9:209–215 (1984).

None of these articles discuss how to clear both the blood vessels and the extravascular space of binding molecules prior to administering the imaging agents, while retaining, attached to the target tissue, as much as possible of the binding molecules. When administering toxins or therapeutic agents, it is even more important to clear binding molecules from the extravascular space (as well as from the blood vessels) so that excess toxin is not bound by the binding molecules in the extravascular space and does not cause damage. Thus, if bispecific binding molecules with one specificity for the target site and one for the toxin/therapeutic agent are administered initially, those molecules which bind to the target site must be retained as much as possible, and those molecules which are unbound and in the circulation or extravascular space should be removed. It is also important that the removal should be accomplished quickly enough so that the binding molecule is not released from the target site before the toxin/therapeutic agent is administered.

A number of factors must be considered in designing an effective method of treating solid tumors using tissue-specific recruiting by a binding molecule of a therapeutic agent. These factors include:

1) the pharmokinetic properties of the binding molecules, therapeutic agents, and other substances used in the method;
2) the clearance routes (reticuloendothelial system versus kidney) of the binding molecules, therapeutic agents and other substances;
3) the diffusion rates of the binding molecules and therapeutic agents in and out from the capillaries;
4) the binding molecules must not be endocytosed by the cells;
5) the on/off times of the binding molecules on the target cells;
6) the affinity of the binding molecules for the therapeutic agents, and the efficiency with which they can recruit the therapeutic agents to the target site;
7) the therapeutic cytotoxins such as ricin A chain, pokeweed antiviral peptide, must enter the target cells to render effects, whereas some other therapeutic substances (and imaging agents) need not enter the target cells to be effective;
8) the immunogenicity and antigenicity of the binding molecules and the therapeutic agents.

These factors make designing an effective method very complex.

SUMMARY OF THE INVENTION

The invention includes using bifunctional two-domain binding molecules to recruit a therapeutic agent to a solid tissue target site, where the binding molecules have one specificity for the target site and the other specificity for the therapeutic agent. The therapeutic agent is administered separately, after administering the binding molecules and after administering a remover substance.

The remover is preferably a liposome which is conjugated with antibodies against the binding molecules. The remover cannot diffuse into the extravascular space and is rapidly removed by the phagocytic cells in the liver, spleen and blood circulation. It binds to binding molecules which are in the circulation, which thereby facilitates the clearing of the binding molecules from the circulation. After clearance, there is a concentration difference in binding molecules across the blood vessel wall, and binding molecules in the extravascular space diffuse into the blood vessels.

The remover should be administered as soon as possible after the binding molecules reach a maximum concentration in the vascular space. When administered at such time, substantial amounts of binding molecule have not yet been released from the target tissue site.

The remover is preferably administered at least twice, and the subsequent administrations of the remover are at a time after the binding molecules in the circulation and extravascular space have reached equilibrium. The administration of remover effectively clears the majority of the binding molecule in both the extravascular space and in the circulation, and will therefore further increase the ratio of binding molecules in the target site over binding molecules in the circulation and extravascular space.

The therapeutic agent should be administered after the last administration of the remover, and after the remover has had enough time to clear from the circulation. But the therapeutic agent should be administered before substantial amounts of binding molecules are released from the target site, so that as much of the therapeutic agent as possible will be bound at the target tissue site by the binding molecules.

The bifunctional two-domain binding molecules are preferably two $V_H$–$V_L$ single-chain binding molecules which are joined together. They can be joined with a linking peptide, as described in U.S. Pat. Nos. 5,132,405 and 5,091,513. See, e.g., FIG. 2D. It is possible to design the remover to include anti-idiotype antibodies which recognize one or more of the binding sites of the binding molecules. In a preferred embodiment, however, an antibody conjugated to the remover recognizes an antigenic structure associated with the joining region between the two $V_H$–$V_L$ single-chain binding molecules, or the antibody recognizes the linking peptide itself Alternatively, the peptide joining the two $V_H$–$V_L$ single-chain binding molecules may be glycosylated, and may have a non-glycosylated peptide or hapten attached thereto. The non-glycosylated peptide is specifically recognized by the antibodies associated with the remover.

It is also preferred, for those therapeutic agents which must enter the cell in order to be effective, that they be linked to a peptide blocker which prevents the therapeutic agent from entering a cell. The blocker is preferably bound by the binding molecules.

The preferred means for linking such therapeutic agents with a blocker is with a hydrophobic, lipophillic peptide linker, such as that described in U.S. Pat. No. 5,149,782. There should also be a cleavage site between the blocker and the therapeutic agent, so that the blocker can be cleaved and allow the therapeutic agent to enter the cell.

The immunoconjugate of the therapeutic agent, the linker and the blocker should be small to minimize the phagocytosis by reticuloendothelial system ("RES") cells. Preferbly, during the time the blocker is bound at the target site by the binding molecules, the blocker will be cleaved and released. The hydrophobic, lipohillic linker will tend to blend with the cell membrane, and thereby enhance the entry of the therapeutic agent into the cell.

The invention will now be described in further detail with reference to the drawings.

DETAILED DESCRIPTION OF THE INVENTION

In the preferred mode of the invention, therefore, three different substances are introduced in three phases. First, bifunctional two-domain binding molecules, with one specificity for antigens at the target site and one specificity for an antigenic site on the therapeutic agent, are administered and allowed time to bind to the target site and to reach a maximum concentration in the extravascular space. The concentrations of the binding molecules in the extravascular space can be monitored by assaying the binding molecules in fluid samples drawn from the peritoneal cavity. Once the binding molecules reach maximum concentration in the extravascular space, a remover substance, preferably a liposome conjugated with antibodies, is administered to remove excess binding molecules from the circulation. This creates a difference in binding molecule concentration across the blood vessel wall. The binding molecules in the extravascular space will tend to diffuse into the blood vessels, where they will also be bound by the remover substance.

The remover is preferably re-introduced several times, each introduction being immediately after the binding molecules reach equilibrium across the blood vessel wall. Each introduction of remover depletes the binding molecules in the blood vessel, because once the binding molecules are bound by the remover they are more easily and rapidly cleared by the RES. The lowered concentration of binding molecules in the blood vessels causes diffusion of the binding molecules from the extravascular space into the blood vessels, resulting in a continuous decrease in the concentration of binding molecules in the blood vessel and the extravascular space. Because the binding molecules are not conjugated with the therapeutic cytotoxin, the uptake and removal of the binding molecules by RES does not poison the cells.

A therapeutic agent is then administered, preferably immediately after the last administration of remover and before any significant amount of the binding molecules are released from the target site. The therapeutic agent is bound at the target site by the binding molecules, which have one specificity for an antigenic site associated with the therapeutic agent.

It is preferred if the entire procedure is completed in eight hours or less. This is a short enough time to prevent substantial amounts of binding molecules from releasing from the target site before the therapeutic agent is administered.

In conventional immunotoxin therapy, the immunotoxin conjugate made up of the antibody and the toxin must be endocytosed by the target cell to kill the cell. One important difference of the present invention is that the bifunctional two-domain binding molecules of the present invention must not be endocytosed by the target cells. If the binding molecules of the invention are endocytosed, they will not be available to bind the therapeutic agent when it is administered.

The bifunctional two-domain binding molecules avoid endocytosis by the target cells because they have only one valency for the tumor-associated antigen, and thus should not induce cross-linking of the antigen. Cross-linking generally will induce endocytosis.

The advantages of the invention include that fact that it maximizes the amount of binding molecule which is at the target site at the time the therapeutic agent is administered, and thereby maximizes the amount of therapeutic agent which reaches the target site. This is achieved through use of small bifunctional two-domain binding molecules and proper timing of the administration of the remover and the therapeutic agent.

The small bifunctional two-domain binding molecules diffuse relatively quickly through the capillary walls, so that administering the remover effectively clears both the circulation and the extravascular space of excess binding molecules before significant amounts of the binding molecules can be released from the target site. This results in less toxicity to the reticuloendothelial cells and other cells in the circulation, and less toxicity to the phagocytic cells in the liver, because the therapeutic agent is bound at the target site and does not circulate or get absorbed in undesired locations.

The preferred binding molecules have the following properties:

1) They have a very high affinity for the target-site surface antigen, with a Ka above $1\times10^9$ $mole^{-1}$;
2) They have a very high affinity for the therapeutic agent, with a Ka above $1\times10^9$ $mole^{-1}$;
3) They have relatively fast kinetic properties, i.e., they reach equilibrium between the blood vessel and the extravascular space relatively quickly (time "$t^{ev}{}_{max}$" in FIGS. 1 and 2 is relatively short);
4) They are not appreciably endocytosed by the target cells, after they bind to the target cells' surface antigen.

The preferred bifunctional two-domain binding molecules for use with the invention are two $V_H$–$V_L$ single chain binding molecules joined together, as described in U.S. Pat. Nos. 5,132,405 and 5,091,513, and as schematically shown in FIG. 7. For binding molecule 30 of FIG. 7, a linker 32 joins the one $V_H$–$V_L$ single-chain binding domain 34 to the other $V_H$–$V_L$ single-chain binding domain 36.

Single-chain $V_H$–$V_L$ binding molecules (as distinct from the two single chain binding molecules of the invention) consist of the Fv portion of an antibody light and heavy chain linked together, typically with a short peptide chain. See U.S. Pat. No. 4,946,778. In the invention, with two single-chain $V_H$–$V_L$ binding molecules joined together, one of the single-chain binding molecules is specific for a target site antigen, and the other is specific for an antigenic site associated with the therapeutic agent.

Two single-chain $V_H$–$V_L$ binding molecules joined together are preferred with the invention because: they are cleared from the circulation more quickly than larger bispecific antibodies or other larger fragments; they are small enough to readily pass across the capillary walls, which allows them to reach equilibrium quickly after administration of the remover substance and before appreciable amounts can release from the target site. Each time they reach equilibrium more remover is administered, and the removal of any unbound binding molecules from the circulation and extravascular space is thereby enhanced.

The linker which joins the two $V_H$–$V_L$ binding molecules should not be an α-helix or β-sheet peptide. These peptides are rigid and hold the two single chain binding sites in one particular orientation, which may not be a suitable orientation for binding. However, the linker should hold the single chain binding sites separated from each other, so that they do not interfere with each other's binding.

The preferred linker for the two $V_H$–$V_L$ binding molecules is a small non-autologous hydrophilic peptide, preferably of about 10 to about 15 amino acid residues in length. Such a non-autologous linker can provide an antigenic site for the antibody conjugated with the remover substance.

More preferably, the peptide contains primarily glycine and/or serine residues, and most preferably, it has glycine and serine residues plus a glycosylation sequence. One glycosylation sequence is Asn-X-Y where "X" can be most amino acids and "Y" is serine or threonine. See Marshall, R. D., *Glycoproteins* p. 679 (1972). Where the peptide is glycosylated, it is most preferable for it to be an autologous peptide that is not immunogenic, and that an antigenic peptide be attached to the carbohydrate moeity.

Glycine or serine residues are preferred because they are usually associated with non-rigid peptides, and do not excessively restrict the orientation of the binding sites. But these residues create a hydrophilic peptide, and the hydrophilicity aids in holding apart the $V_H$–$V_L$ binding sites so that they do not interfere with each other and inhibit binding. Glycosylated peptides are more preferred because the carboydrate adds additional hydrophilicity to the linker, which helps to physically separate the two binding domains.

Figure 8:
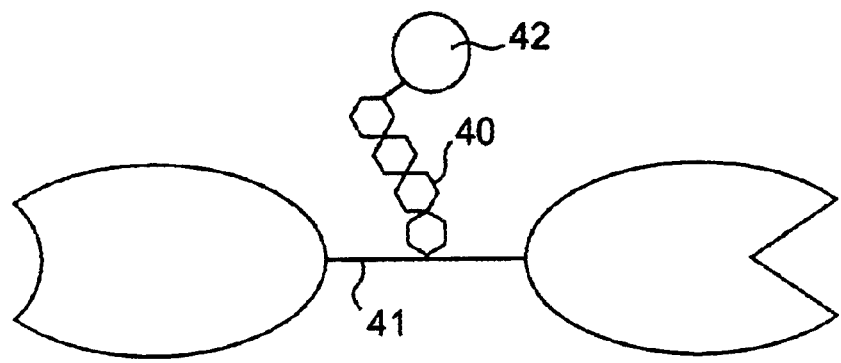
FIG. 8 shows the bifunctional two-domain binding molecule of FIG. 8 with an antigenic peptide attached to the glycosylated chain on the linker.

It is preferred that the remover binds to the linker rather than to another portion of the binding molecule. Thus, in the preferred embodiment shown in FIG. 8, the carbohydrate moiety 40 of the linker 41 is conjugated with a hapten or a non-autologous peptide 42 of about 6 to 10 amino acids in length. Peptide 42 provides an antigenic site for the antibody associated with the remover.

The preferred remover substance has the following properties:
1) It can specifically bind to the binding molecules;
2) It remains in the circulation and does not diffuse through the holes in the capillary wall and into the extravascular space or into solid tissues, except that it does diffuse into the spleen, liver and lymphoid tissues;
3) It is rapidly cleared by the reticuloendothelial system.

The preferred remover is a liposome which is conjugated with antibodies specific for an antigenic site associated with the peptide which joins the two bifunctional binding molecules together. However, the antibodies can also be specific for any portion of the linked $V_H$–$V_L$ binding molecules, or they can be anti-idiotypes to the $V_H$–$V_L$ binding molecules. The antibodies can also be conjugated to a polymeric substance, such as dextran or polyethylene glycol.

Figure 1:
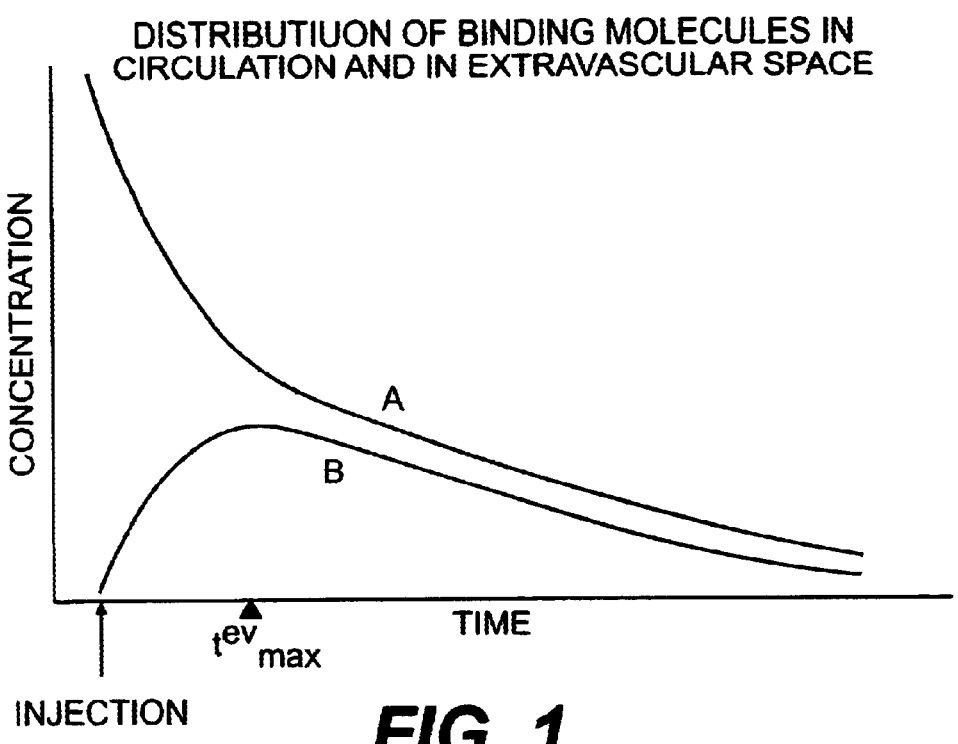
FIG. 1, which plots binding molecule concentration in the circulation against time, shows the kinetics of binding molecule concentration in the circulation and the extravascular space, after intravenous administration.
Figure 2:
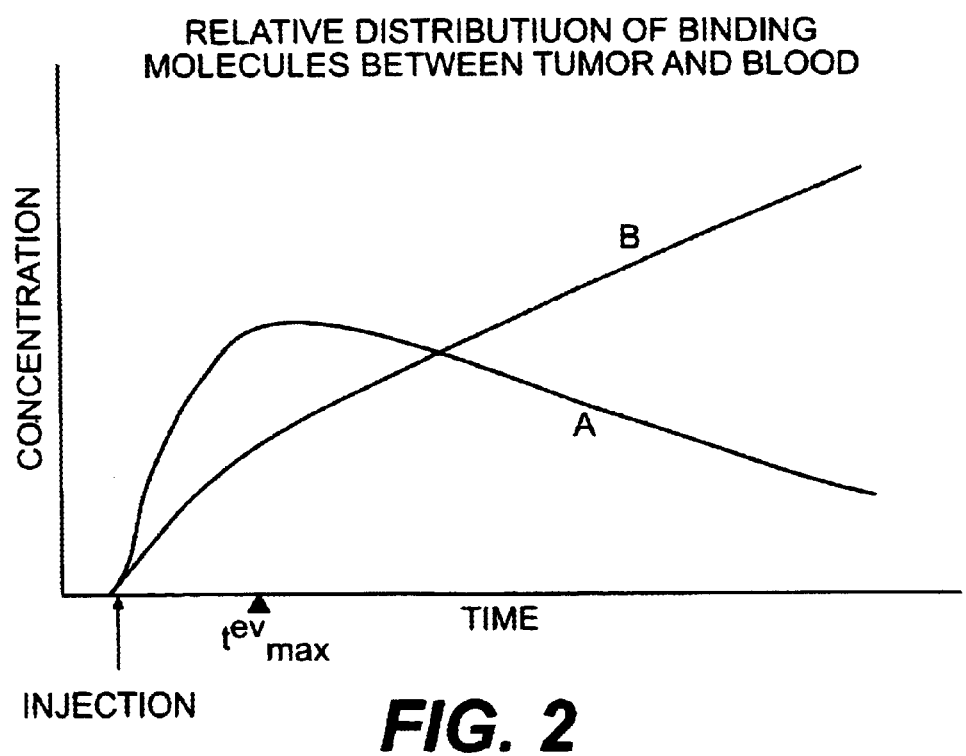
FIG. 2 shows the kinetics of binding molecule concentration at the tumor site and in the circulation, after intravenous administration.

Referring to FIGS. 1 and 2, the pharmokinetics of a binding molecule which has been administered is illustrated. Curve A in FIG. 1 represents the concentration of binding molecule in the blood circulation, and curve B represents the concentration in the extravascular space. Curve A shows a rapid decline after injection to time $t^{ev}_{max}$, representing the time during which binding molecules diffuse into the extravascular space and are bound at the target site. After time $t^{ev}_{max}$, curve A declines more slowly, representing the clearance of the binding molecules by the reticuloendothelial system, the kidneys and other cells of the body.

Referring to curve B in FIG. 1, it can be seen that the concentration of binding molecule in the extravascular space increases after injection to $t^{ev}_{max}$, when equilibrium between the blood circulation and the extravascular space is reached.

FIG. 2 represents the kinetics of distribution of the binding molecules between the tumor and the blood. Curve A represents the amount of binding molecule associated with the target antigen. It increases rapidly from injection to time $t^{ev}_{max}$, and then declines slowly thereafter, the latter phase representing the time during which binding molecules are releasing from the target site. Curve B represents the tumor/blood concentration ratio. It can be seen that this ratio increases slightly more rapidly from injection to time $t^{ev}_{max}$ than the increase after time $t^{ev}_{max}$.

When the binding molecules administered are smaller, the pharmokinetic consequences are as follows:
1) the time to $t^{ev}_{max}$ is shorter;
2) the concentration difference between the blood and the extravascular space is smaller;
3) the concentration of the binding molecules in the extravascular space can reach higher levels;
4) more of the binding molecules can be bound at the target site;
5) the binding molecules diffuse more quickly from the extravascular space to the blood circulation.

Because all these consequences are advantageous, the preferred binding molecules are two single-chain $V_H$–$V_L$ binding molecules joined together. Such joined single chain binding molecules are smaller than many antibody fragments, such as F(ab')$_2$ fragments, and smaller than whole antibodies.

Figure 3:
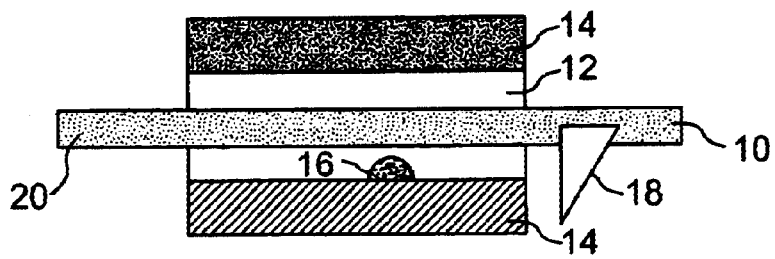
FIG. 3 is a schematic representation of a blood vessel sorrounded by an extravascular space which is in turn contacted by solid tissue. The solid tissue has a tumor thereon, as indicated. The liver is shown schematically as fluidly linked with the blood. Binding molecules (the solid dots inside the blood vessel) have been administered.

The clearance of binding molecules at different points in time in relation to the administration of the remover is illustrated in FIGS. 3–7. FIG. 3 schematically shows a blood vessel 10 surrounded by extravascular space 12 which is in turn contacted by solid tissue 14. The solid tissue 14 has a tumor 16 thereon, which is a target site for the binding molecules 20. The liver 18 is shown fluidly linked with the blood vessel 10. Binding molecules 20 have recently been administered and are still all within the blood vessel 10.

Figure 4:
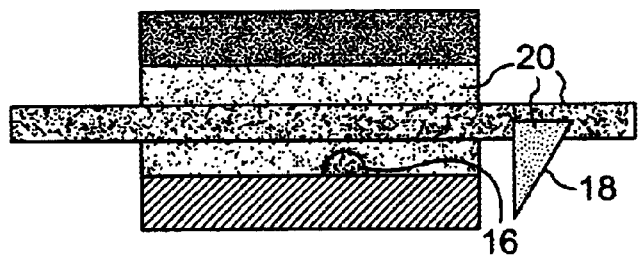
FIG. 4 is the same shematic representation as in FIG. 3, but at a later time when the binding molecules have reached a maximum concentration in the extravascular space.

FIG. 4 shows the same view as FIG. 3, shortly thereafter. FIG. 4, represents time $t^{ev}_{max}$, of FIGS. 1 and 2, at which the binding molecules 20 reach a maximum concentration in the extravascular space 12 as the equilibrium between the extravascular space 12 and the inside of the blood vessel 10 is reached. The binding molecules 20 also bind to the target site at near maximum levels. Some of the binding molecules 20 have been absorbed and taken up by the liver 18.

Figure 5:
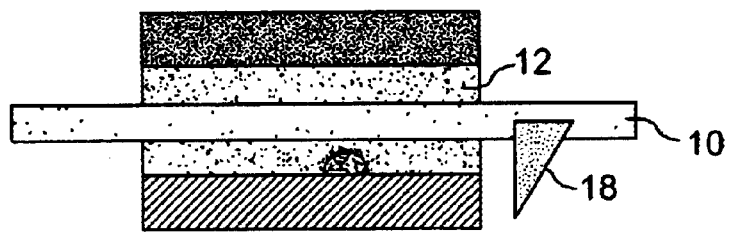
FIG. 5 is the same shematic representation as in FIG. 4, but after administration of remover substance.

FIG. 5 is at a later time, after a remover has been administered. As a result of the remover substance's action, the concentration of the binding molecules 20 in the blood vessel 10 is greatly reduced. Because the rate of diffusion of the binding molecules 20 across the capillary wall is slower than the rate of clearance of the remover by the RES, the concentration of binding molecules 20 is higher in the extravascular space 12 than in the blood vessel 10. The amount of binding molecules 20 bound by tumor 16 remains near maximum levels. More of the binding molecules 20 have been taken up by the liver 18.

Figure 6:
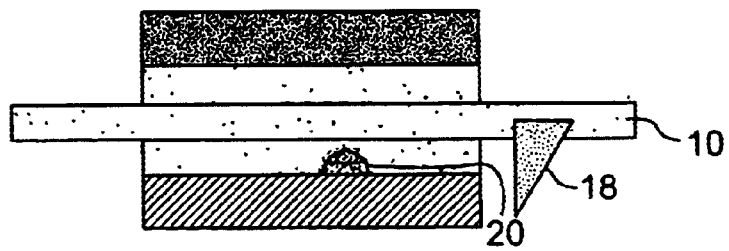
FIG. 6 is the same shematic representation as in FIG. 5, but at a later time after much of the binding molecules have cleared from the circulation.
Figure 7:
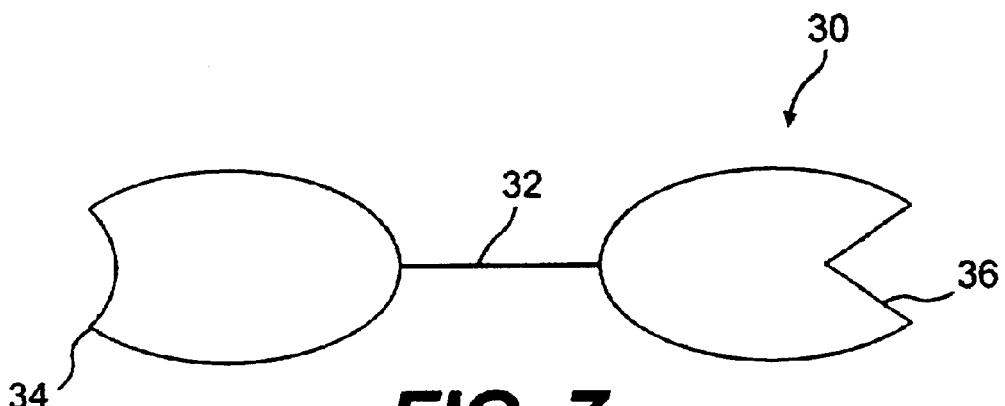
FIG. 7 is a schematic representation of a bifunctional two-domain binding molecule, suitable for use with the invention.

FIG. 6 is at a still later time, after the binding molecule removal phase is substantially complete. Little of the binding molecules 20 remain in the blood vessel 10 or in the extravascular space 12. The amount of binding molecules 20 bound by the tumor 16 remains at about the same level as in FIG. 5, because the release time of the binding molecules is much longer than the time needed for the binding molecules to diffuse into the blood vessel 10 and be removed. The liver 18 has taken up more of the binding molecules 20 and has also digested some of them. The conditions are now optimal for administering the therapeutic agent.

Because the remover is intended to clear the free binding molecules in both the blood circulation and also in the extravascular space, it should be administered repeatedly shortly after the binding molecules reach $t^{ev}_{max}$. It is more preferred if the remover is administered over a total length of time that is about 4–5 times $t^{ev}_{max}$.

The preferred total length of the removal phase of 4–5 times $t^{ev}_{max}$, allows nearly all of the binding molecules to diffuse back into the blood vessels from the extravascular space, and to then be bound in the blood vessels by the remover substance. But such a removal phase is not so long as to allow significant amounts of the binding molecules to release from the target site before the therapeutic agent is administered.

It is preferred if the remover substance is either repeatedly added or is continously infused intravenously. Assuming that at $t^{ev}_{max}$ about one-half of the binding molecules are in the extravascular space (which would result at equilibrium), then after the remover has been administered four times (at $4\times t^{ev}_{max}$), the residual amount of binding molecules in the extravascular space will be about $\frac{1}{2}\times(\frac{1}{2})^4$, or about 3% of the total binding molecules originally administered.

From the available pharmokinetic data about whole IgG, and about F(ab')$_2$ and Fab fragments, it is estimated that $t^{ev}_{max}$ for whole IgG, F(ab')$_2$ and Fab are about 50 hours, 20 hours, and 1 hour, respectively. See LoBuglio, A. F. et al. *Proc. Natl. Acad Sci. U.S.A.* 86:4220–4224 (1989); Moblofsky, P. J. et al. *Radiology* 149:549–555 (1983); Larson, S. M. et al. *Radiology* 155:487–492 (1985). The two joined single-chain $V_H$-$V_L$ binding molecules preferred for use with the invention are about the same size and have a similar overall structure to Fab fragments. Thus, these binding molecules should have about the same difussion rate and $t^{ev}_{max}$ as the Fab fragments. Based on a $t^{ev}_{max}$ of 1 hour with the preferred binding molecules, the total time to complete administration of the binding molecules, the remover substance and the therapeutic agent is about 6 hours.

Bifunctional IgG or F(ab')$_2$ are not preferred for use with the invention because their diffusion rates are slow and their $t^{ev}_{max}$ is long. By the time the free binding molecules in the circulation and in the extravascular space are cleared by the remover agent (a period of several times $t^{ev}_{max}$), significant amounts of binding molecule will have released from the target site. Thus, not as much of the therapeutic agent will be bound at the target site as when using the preferred binding molecules.

The remover substance is cleared from the circulation at a considerably faster rate than the binding molecules diffuse into the blood vessels. Thus, after each administration of remover, the binding molecules are present in the circulation in decreasing quantities. It is preferable, therefore, to administer the remover at a decreasing dosage over time, each administration of the remover being after the binding molecules reach equilibrium across the blood vessel walls. Alternatively, the remover may be administered by infusion at a progressively decreasing dosage.

The therapeutic agents are essentially of two types: those which must enter the cell to be effective and those which need not do so. The latter group includes agents which act on cell surface receptors, including cytokines such as tumor necrosis factor ("TNF") and interleukin-1. The former group, which must enter the cell, include cytotoxic or cytolytic substances such as plant or microbial ribosomal-inactivating toxins, including gelonin, abrin, ricin A chain, Pseudomonas exotoxin, diptheria toxin, pokeweed antiviral peptide, tricathecums; anti-sense RNAs that inhibit the expression of tumorigenic proteins.

Those therapeutic agents which must enter the target cells are preferably chemically modified to facilitate their entry into cells. These agents are conjugated with membrane blending agents, such as those described in published U.S. Pat. No. 5,149,782, which are in turn conjugated to blockers.

Figure 9:
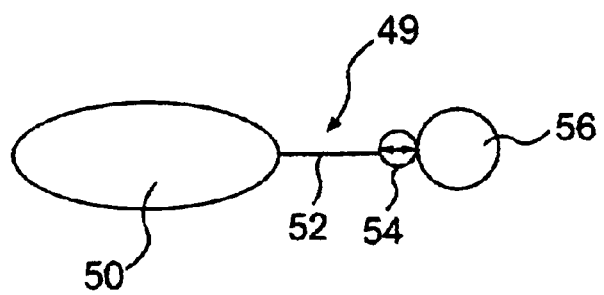
FIG. 9 is a schematic representation of one preferred form of the therapeutic agent, having a therapeutic substance attached with a membrane translocation agent to a blocker.

An exemplary conjugate 49 of a membrane blending agent, blocker and therapeutic agent is schematically shown in FIG. 9. A therapeutic agent 50 is linked by a membrane blending agent 52 to a blocker 56. A cleavage site 54 is on the membrane blending agent 52 adjacent the blocker 56.

Blocker 56 prevents insertion of the membrane blending agent 52 into the cell before the blocker 56 is cleaved. After blocker 56 is cleaved at site 54, membrane blending agent 52 blends with and inserts into the cell membrane, thereby aiding the entry of therapeutic agent 50 into the cell. Thus, therapeutic agent 50 can only enter the target cell after blocker 56 is cleaved.

The preferred membrane blending agent is described in published U.S. Pat. No. 5,149,782. It can be a membrane fusion peptide, a long chain fatty acid, or a membrane channel-forming peptide.

The blocker is described in U.S. Pat. No. 5,149,782 as preferably being an antibody which targets the particular cells sought to be treated. In the present invention there is no need for using an antibody as the blocker, as it is the single chain $V_H$-$V_L$ binding molecules, not the blocker, which are responsible for the tissue-specific recruiting. An antibody blocker may actually be less desired than other types of blockers, as an antibody will be more antigenic and will tend to be cleared faster by the reticuloendothelial system.

The preferred blocker for use in the invention is a hapten or a small antigenic peptide which is bound by one of the $V_H$-$V_L$ binding sites of the binding molecule. This peptide should not be autologous.

A preferred cytotoxin to be used in the present application is ricin A chain, which possesses the ribosome-inactivating activity but not the carbohydrate binding and translocation activities. The latter two activities reside in the B chain. It has been shown that conjugating ricin A chain with long chain fatty acid can greatly enhance the cytotoxic activity in cell culture. Kabanov, A. V. et al. *Protein Engineering* 5:39–42 (1989). Another preferred cytotoxin is the modified or truncated pseudomonas exotoxin A (a single chain protein), which lacks the cell recognition domain but still possesses both the translocation and the ADP ribosylating activity. Kondo, T. et al. *J. Biol. Chem.* 263:9470–9475 (1988). By conjugating the truncated pseudomonas exotoxin A with a membrane blending agent and a blocking agent, the toxin can be delivered to the target site in an inactive form, and once the blocking agent is cleaved at the target site, its affinity for the cell membrane is enhanced. Because the truncated pseudomonas exotoxin still possesses the translocation activity, the toxin can get into target cells to exert cytotoxic effect.

The methods of the invention will be very effective in targeting therapeutic agents to tissues which are outside the circulation and lymphatic systems. The preferred target sites for the therapeutic agents are solid tumors, which are particularly difficult to treat effectively by conventional means. Because the methods of the invention allow the therapeutic agent to be administered a relatively short time after administering the binding molecules, the effects of the therapeutic agent is maximized and its dosage can be minimized, thereby minimizing the toxicity to the kidney and other tissues. Further, because the therapeutic agents are not conjugated to the binding molecules at the time of administration, the therapeutic agents (which are smaller than the binding molecules) can be cleared by the kidney, thereby further reducing the toxicity to the liver and other tissues.

Another advantage of the invention is that the effectiveness of the therapeutic agent depends only on its concentration at the target site. A conventional immunotoxin must be endocytosed for it to be effective in killing target cells. This means that the entire structure, including the antibody and the toxin, must be endocytosed. As noted above, endocytosis is more likely to occur if the antibody can cross-link a target site antigen. However, it is well-known that the density of tumor-associated antigens on the cell surface varies from cell to cell, due to the cell's cycle, antigenic drift, and other factors. Thus, a conventional immunotoxin's effectiveness is limited to the extent to which it is endocytosed.

In contrast, the therapeutic agents of the present invention do not need to be endocytosed to be effective. For those therapeutic agents noted above which must enter the cell to be effective, the membrane blending agent aids their entry into the cell. Cross-linking of a surface antigen is not necessary, and therefore, their effectiveness is not limited by the availability of the cell surface antigens on a particular cell in the tissue site, but only by the total amount of the surface antigen at the tissue site.

Specific examples of making the various components of the invention are described below.

(1) Preparation of Conjugates of a Therapeutic Agent with Membrane Blending Agents and Blockers A preferred therapeutic agent to be used in the form of molecular conjugates of the present invention is ricin A chain, which possesses the ribosome-inactivating activity but not the cell-binding activity of whole ricin molecules. The preparation of three-component molecular conjugates is described in U.S. Pat. No. 5,149,782.

For making these conjugates, a preferred group of membrane blending agents are long chain fatty acids. For convenience, fatty acids of 14, 16 or 18 carbons in length, more preferably having at least one double-bond for addition/substitution reactions, may be used. These fatty acids, namely myristoleic acid, palmitoleic acid, and oleic acid, which all have double bond at $C_9$–$C_{10}$, may be purchased from Matreya, Inc., in Pleasant Gap, Pa. The unsaturated double bond may be subjected to addition/substitution reactions to incorporate one of the many heterobifunctional cross-linking agents (which are available from reagents firms, e.g. Pierce Chemical Co.) using techniques which are routine in organic chemistry.

One possible group of blocking agents are haptens, such as 2, 4, 6-trinitrobenzene and phenylarsonate. Monoclonal antibodies against these hapten blocking agents have already been produced.

A preferred group of blocking agents are short peptides of about 6 to 10 amino acids in length, which do not bear any autologous antigenic epitopes present in humans. The peptides should be resistant to proteolytic digestion in serum and other body fluids. The amino acid sequence may be checked using one of the available programs (e.g., the MICRO GENIE™ program from Beckman Instruments) for homology with the peptide sequence of human proteins, which is available in recently updated database. The peptides derived from proteins of animal or insect or microorganism origin are possible choices. One specific example of a suitable peptide is an eight amino acid segment (SEQ ID NO: 1 Thr-Leu-Pro-Ile-Ala-His-Glu-Asp) from the $CH_2$ domain of rabbit IgG, residues #324–331. Five or six of these eight amino acids are different between this segment and the corresponding segment of human $IgG_1$, $IgG_2$, $IgG_3$, and $IgG_4$.

Depending on the cross-linking agent to be used, a cysteine residue can be added to the N or C-terminal end of the peptide to aid in linking.

(2) Preparation of Monoclonal Antibodies Against Haptens or Short Peptides

In the present invention, monoclonal antibodies specific for haptens or short peptides are of two types:

(1) Monoclonal antibodies specific for the blocking groups of the molecular conjugates of therapeutic agents. These monoclonal antibodies can be re-engineered to make one binding domain of the bifunctional single-chain binding molecules of the invention.

(2) Monoclonal antibodies specific for the antigenic epitopes on the linking peptide of the bifunctional two-domain binding molecules of the invention. These monoclonal antibodies are preferably incorporated into liposomes to make the remover substances of the invention, or they can be conjugated with other larger molecules to make a suitable remover substance.

Monoclonal antibodies specific for haptens or short peptides can be prepared according to routine, standard methods for making hybridomas and monoclonal antibodies, such as the methods described in Kennett, R. H. et. al (Eds.), *Monoclonal Antibodies, Hybridomas*: A New Dimension in Biological Analyses. pp. 363–417 (Plenum Press, New York 1980) or Hudson, L. and Hay, F. C. (Eds.), *Practical Immunology 2nd ed.* (Blackwell Scientific Publications, Boston 1980).

According to the procedures described in these handbooks, the hapten or the peptide can be conjugated to a protein carrier such as keyhole limpet hemocyanin (KLH) at a ratio of multiple peptides (hapten groups) per KLH molecule. Mice are immunized with the conjugate in complete Freund's adjuvant, intraperitoneally, in the first immunization, and in incomplete Freund's adjuvant in 3–4 subsequent immunizations. The spleen cells from the immunized mice are fused with Sp2/0 myeloma cells to produce hybridomas. The antibodies secreted by the hybridomas are screened by ELISA for reactivity with the peptide or hapten coupled to a different protein, such as chicken ovalburnin.

(3) Preparation of Immunoliposomes

Various methods have been established to prepare liposomes and to conjugate IgG to the surface of liposomes. See, e.g., Ostro, M. J. (Ed.), *Liposomes: from Biophysics to Therapeutics* (Marcel Dekker, New York, 1987). One preferred method of preparing liposomes and conjugating IgG to their surface is described by Ishimoto, Y. et al., *J. Immunol. Met.* 75, 351–360 (1984). Multilamillar liposomes composed of dipalmitoylphosphatidylcholine, cholesterol and phosphotidyletbanolamine are prepared. Purified IgG monoclonal antibody (or a fragment thereof) can then be coupled to the phosphatidylethanolamine by the cross-linking agent N-hydroxysuccinimidyl 3-(2-pyridyldithio) propionate. The coupling of the antibody to the liposome can be demonstrated by the release of a pre-trapped marker, e.g., carboxyfluorescence, from the liposomes upon the treatment of secondary antibody against the conjugated antibody and complement.

(4) Making Two Linked Single Chain $V_H$–$V_L$ Binding Molecules

U.S. Pat. Nos. 5,132,405 and 5,091,513 discloses how to splice framework and complementarity determining regions into single chain $V_H$–$V_L$ binding molecule. See especially U.S. Pat. No. 5,091,513; col. 9, line 43 to col. 12, line 45. As noted therein, the $V_H$–$V_L$ binding molecule can be cloned into the plasmid pUC8 and expressed in *E. coli*.

U.S. Pat. Nos. 5,132,405 and 5,091,513 also discloses how to design and make a linker for the single chain $V_H$–$V_L$ binding molecule. See especialy U.S. Pat. No. 5,091,513; col. 18, line 6 to col. 19, line 31. This can then be used to express a complete linked single chain $V_H$–$V_L$ binding molecule.

Essentially the same procedures as described in U.S. Pat. Nos. 5,132,405 and 5,091,513 can be used to link two single chain $V_H$–$V_L$ binding molecules together to make the binding molecules of the invention. As noted in U.S. Pat. Nos. 5,132,405 and 5,091,513, a peptide linker of appropriate length can be designed based on the desired distance needed between each $V_H$–$V_L$ binding molecule to prevent steric hindrance or shielding of the binding sites. U.S. Pat. Nos. 5,132,405 and 5,091,513 also describes how to prepare nucleotides coding for the linker and the single chain $V_H$–$V_L$ binding molecule. Similar techniques could be used to prepare the nucleotides for coding the linker between the two single chain $V_H$–$V_L$ binding molecules of the invention.

Numerous monoclonal antibodies against tumor-associated surface antigens in human pancreatic and colorectal cancers (e.g., antibody 17-1A), ovarian cancer (e.g., antibody against CA125), liver cancer (e.g., anti-CEA), breast cancer (e.g., monoclonal antibody 72.3), melanoma (e.g., antibody 48.7 against HMWA antigen), as well as against many other tumors, have been developed. Many of these antibodies have been well known in the field of human tumor immunotherapy and have been studies in human clinical trials. Cell lines derived from the tumorous tissues have also been developed. In one very useful animal model using nude mice, the human tumor cell lines, when transplanted to the mice, develop tumors. Thus, a candidate therapeutic antibody or binding molecule can be used experimentally in the mouse model.

For constructing a two binding domain single chain binding molecule, one of binding domain can be derived from the Fv of one of these anti-tumor surface-antigen antibodies. The other domain can be derived from the Fv of an antibody specific to the blocking agent of the therapeutic agent described above. The cloning and the sequencing determination of the VH, $V_L$ of these antibodies can be performed by routine molecular biology techniques.

A preferred specific sequence of a linker between the two binding domains of the single chain binding molecules of the present invention should contain a nonautologous segment. An example is:

Gly-Gly-Ser-Thr-Pro-Ser-Pro-Gly-Ile-Gln-Val-Ser-Gly-Gly SEQ ID NO: 2

The underlined portion of eight amino acids is a segment in the CH3 domain of rabbit $\mu$ chain (#362–369). Six of eight amino acid residues are different from the corresponding segment in human $\mu$ chain. The flanking Gly and Ser residues are for increasing the total length to 14. The sequence does not contain glycosylation site and the entire DNA encoding the two binding domains and this linker can thus be expressed in *E. coli*.

Another preferred linker is a glycosylated form. The peptide portion contains a glycosylation site. One example of this linker is:

Gly-Gly-Ser-Asn-Gly-Ser-Gly-Gly-Asn-Gly-Thr-Gly-Ser-Gly SEQ ID NO: 3

The sequence contains two potential N-glycosylation sites (underlined). The Gly and Ser residues enhance the flexibility and non-rigid conformation of the linker.

The DNA encoding the two binding domains and the linker should be expressed in mammalian cells, such as CH0 cell line, which can add the carbohydrate moeity to the glycosylation sites. One preferred expression system to be used in a CH0 cell line for the expression of immunoglobulin genes is the method described by Page, M. J. and Sydenham, M. A. *Bio/Technology* 9:64–68 (1991).

In the following section, the conjugation of a hapten or a peptide to a carbohydrate moeity is described. The eight amino acid peptide described in this section can be used for conjugation to the carbohydrate moeity.

(5) Conjugation of an Antigenic Peptide or Hapten to the Carbohydrate Site of Two Linked Single Chain $V_H$–$V_L$ Binding Molecules The preferred method of conjuating an antigenic peptide or hapten to the carbohydrate site of two linked single chain $V_H$–$V_L$ binding molecules is adopted from the procedures described by O'Shannessy, D. J. et al., *Immunol. Lett.* 8:273–277 (1984) and Rodwell, J. D. et al., *Proc. Nat'l. Acad. Sci. U.S.A.* 83:2632–2636 (1986). The principle is to generate reactive aldehydes on the sugar moieties by sodium periodate treatment, and to link a reactive hydrazide group of the bifunctional linking group to the hapten or peptide to be conjugated and then to couple the two reactants.

This procedure has been applied successfully to conjugate antigenic peptides and haptens to a number of different IgG and IgM monoclonal antibodies. For example, these techniques have been used by Cytogen Corp. to make immunoconjugates for imaging tumors in vivo, which are now pending FDA approval.

The terms, expressions and examples herein are exemplary only and not limiting, and those skilled in the art will recognize, or be able to ascertain using no more than routine experimentation, many equivalents to the specific embodiments of the invention described herein. All such equivalents are encompassed by the following claims.

What is claimed is:

1. A method of enhancing delivery of a therapeutic agent selected from the group consisting of tumor necrosis factor and interleukin 1 to a solid tissue site, comprising:

administering to a patient a conjugate consisting of two individual single chain $V_H$-$V_L$ binding molecules which are conjugated with a hydrophilic peptide linker, one single chain binding molecule having specificity for a solid tissue antigen and the other for the therapeutic agent, and waiting until the conjugate concentration in the extravascular space reaches equilibrium between the extravascular space and the capillaries;

administering a liposome conjugated with antibodies specific for the conjugate which binds circulating conjugate;

administering the therapeutic agent.

2. The method of claim 1 further including the step of administering the liposome conjugated with antibodies at least one more time after time is allowed for the conjugate in the extravascular space and the blood circulation to reach equilibrium.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 8 amino acids
        (B) TYPE: amino acid
        (D) TOPOLOGY: Linear (xi) SEQUENCE DESCRIPTION: SEQ ID NO:1:

Thr Leu Pro Ile Ala His Glu Asp
1               5

(2) INFORMATION FOR SEQ ID NO:2:

(i) SEQUENCE CHARACTERISTICS:
        (A) LENGTH: 14 amino acids
        (B) TYPE: amino acid
        (D) TOPOLOGY: Linear (xi) SEQUENCE DESCRIPTION: SEQ ID NO:2:

Gly Gly Ser Thr Pro Ser Pro Gly Ile Gln Val Ser Gly Gly
1               5                   10

(2) INFORMATION FOR SEQ ID NO:3:

(i) SEQUENCE CHARACTERISTICS:
        (A) LENGTH: 14 amino acids
        (B) TYPE: amino acid
        (D) TOPOLOGY: Linear (xi) SEQUENCE DESCRIPTION: SEQ ID NO:3:

Gly Gly Ser Asn Gly Ser Gly Gly Asn Gly Thr Gly Ser Gly
1               5                   10